United States Patent [19]

Schneider

[11] 4,102,343

[45] Jul. 25, 1978

[54] LIGATURE MECHANISM FOR PRODUCING TOURNIQUET EFFECTS ON LIMBS

[75] Inventor: Eberhard Schneider, Cologne, Fed. Rep. of Germany

[73] Assignee: Prameta Prazisionsmetall-und Kunststofferzeugnisse G. Baumann & Co., Fed. Rep. of Germany

[21] Appl. No.: 709,245

[22] Filed: Jul. 27, 1976

[30] Foreign Application Priority Data

Aug. 16, 1975 [DE] Fed. Rep. of Germany ....... 2536620
Sep. 17, 1975 [DE] Fed. Rep. of Germany ....... 2541433

[51] Int. Cl.² .............................................. A61B 17/12
[52] U.S. Cl. ........................................ 128/327; 24/78; 24/191
[58] Field of Search ............... 24/77 R, 77 S, 78, 191, 24/170; 128/326, 327, 134

[56] References Cited

U.S. PATENT DOCUMENTS

| 405,962 | 6/1889 | Kennedy | 24/78 |
| 510,918 | 12/1893 | Kaiser | 24/78 |
| 2,882,903 | 4/1959 | Ramien | 128/327 |
| 3,425,104 | 2/1969 | Mochizuki | 24/78 X |
| 3,958,575 | 5/1976 | Von Soiron | 128/327 |

*Primary Examiner*—Robert W. Michell
*Assistant Examiner*—Michael H. Thaler

[57] ABSTRACT

This invention relates to a novel ligature mechanism for producing tourniquet effects on limbs including a casing having pivotally mounted therein a clamping lever which locks upon a first end portion of a band which passes through an aperture of the casing, a medial portion of the band forming a loop adapted to encompass a limb, a second end portion of the band carrying a fitting, and spring means releasably clampingly securing the fitting to either the lever or to the casing. Releasing means formed integral with or apart from the fittng is provided for actuating the spring to release the second end portion from either the lever or the casing.

18 Claims, 13 Drawing Figures

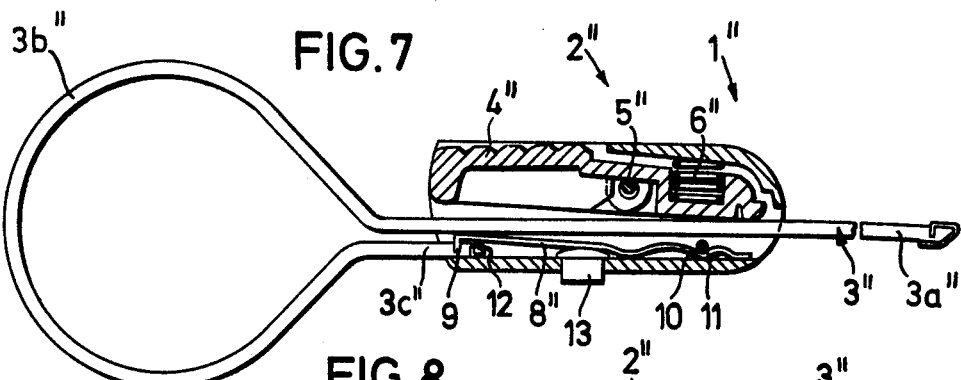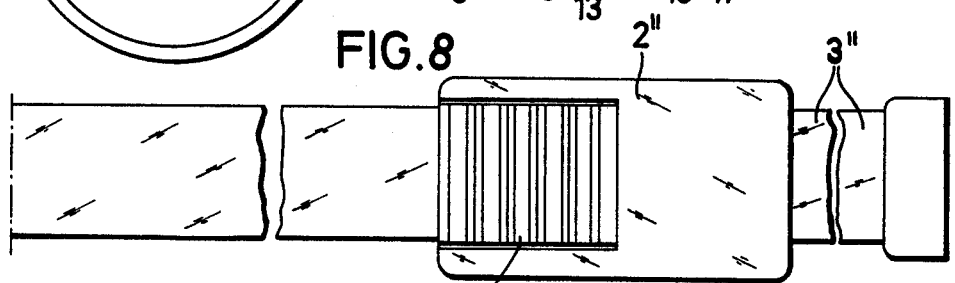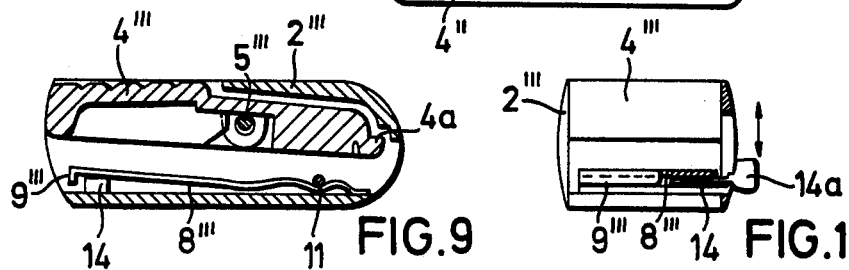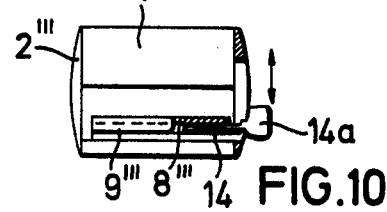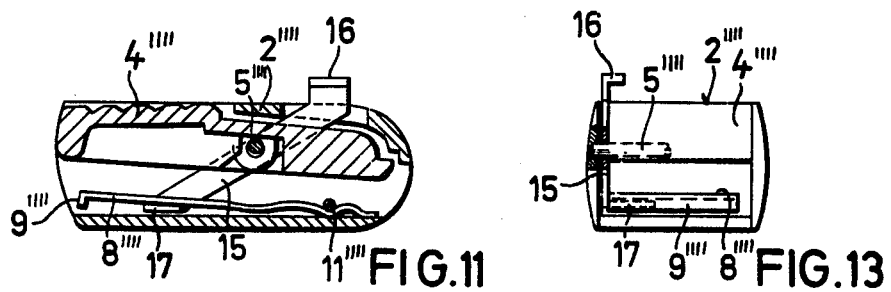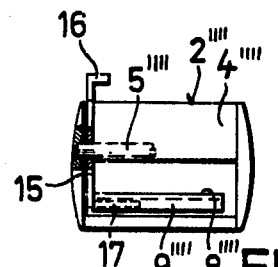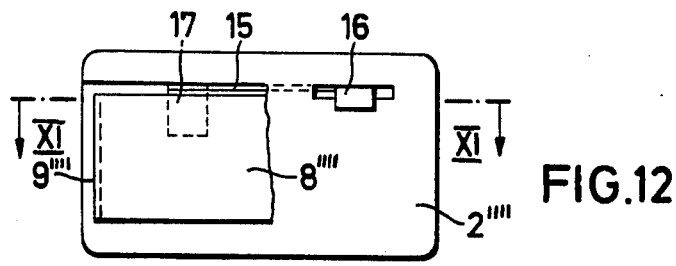

LIGATURE MECHANISM FOR PRODUCING TOURNIQUET EFFECTS ON LIMBS

The present invention relates to a ligature for producing tourniquet effects on limbs of humans and/or animals and is of the type including a housing or casing which is combined with a band defining a loop which can be tightened relative to a limb.

In ligature mechanisms of the type to which this invention is directed, the band generally is so arranged that both ends thereof pass through the casing and either or both are pulled to tighten a loop portion of the band about a limb. However, irrespective of the particular construction of the ligature or ligature mechanism, it is highly desirable in such mechanism that the loop be rapidly and reliably opened in order to remove the band from the limb. This is necessary in order that the ligature not be simply drawn along the limb because, for example, there may be encountered such obstacles as, for example, an inserted syringe. Thus, it is important that the loop of the ligature be rapidly and readily applied to and removed from a limb.

Ligatures are also known in which the casings or housings thereof are formed of two or three parts. One part generally includes a clamping lever which can be operated to clamp or unclamp one or both of the end portions of the band as either or both pass through the casing for tightening or loosening the loop. More often than not, one end of the band is attached to the closure and the opposite end is the only end clamped to the closure by the clamping lever. The clamping lever is generally operated by a locking and unlocking device and thus the overall construction is relatively complex. Moreover, in such conventional ligatures, the band is generally attached to the casing by screws or rivets which makes the band difficult to remove which may be desirable for purposes of cleaning.

Ligatures are also known in which the band may be readily releasably attached to the casing, but generally such attachments are complicated and costly from a standpoint of manufacture. The end of the band which is to be secured to the casing is generally riveted or screwed to a fork-shaped part (male element) whose legs engage in a slide (female element) which must be shifted transversely of the casing in order to release the band. Tilting or jamming during release or assembly can occur and any sudden release of the band from the casing is obviously highly undesirable.

In keeping with the foregoing, it is a primary object of this invention to provide a novel ligature mechanism in which one end of a band is readily and reliably snap-secured to either the clamping lever or the casing, and this is preferably accomplished by means of a leaf spring which clampingly secures a fitting connected to a terminal end of the band between an abutment of the clamping lever and the leaf spring or simply providing the leaf spring with a locking nose which cooperates with the band fitting to lock the same to the housing.

In further accordance with this invention, the fitting may be either of a one-piece or two-piece construction, and in either event the fitting itself includes means for releasing the fitting from between the spring and the abutment means in the form of a tab or projection directed toward the loop of the band which precludes accidental release of the band while the tourniquet effect is being applied.

In keeping with the embodiment of the invention in which the fitting of the band is carried by the clamping lever in projection of the fitting is obliquely disposed in a direction toward the loop such that in order to release the tourniquet effect, the clamping lever is depressed and the tab, should it press against the limb of a patient will automatically cause the release of the band from its confinement between the abutment means and the spring.

A further desirable feature in keeping with the present invention is that the connection between the fitting and the clamping lever is such that upon the release of the fitting the same springs off in a downward direction which has the advantage that the band will reliably avoid interfering with the injection needles and the like in the limb of a patient when the ligature mechanism is being removed.

In further keeping with this invention, the lever includes a downwardly opening recess into which the fitting of the band is received and the spring is disposed transversely of the clamping lever in a bowed fashion such that the fitting is accurately located within the recess between the spring and the abutment means. Alternately, the leaf spring may be of a generally Z-shaped configuration with a free terminal end thereof curving toward a bottom wall of the casing whereby only intentional depression of the release mechanism or tab, formed integrally with or as a separate component of the fitting, will disengage the fitting by the deflection of the spring.

With the above and other objects in view that will hereinafter appear, the nature of the invention will be more clearly understood by reference to the following detailed description, the appended claimed subject matter, and the several views illustrated in the accompanying drawings.

IN THE DRAWINGS:

FIG. 7 is a longitudinal sectional view of another ligature mechanism of this invention, and specifically illustrates a spring secured to a bottom wall of a casing at one end thereof with an opposite end clampingly securing an end of the band to a lower wall of the casing.

FIG. 8 is a top plan view of the ligature mechanism of FIG. 7 and illustrates the exposed area of the clamping lever which is depressed to release the band.

FIG. 9 is a longitudinal sectional view through a casing similar to that associated with the ligature device of FIG. 7, and illustrates a mechanism for releasing an associated leaf spring.

FIG. 10 is a side elevational view with a portion broken away of the casing of FIG. 9, and illustrates a button which can be raised to release the leaf spring.

FIG. 11 is a longitudinal sectional view of another casing similar to that shown in FIGS. 7 and 9, and illustrates a pivotally mounted lever for releasing an associated leaf spring.

FIG. 12 is a top plan view of the casing of FIG. 11 with a portion thereof broken away for clarity and illustrates a portion of the lever projecting through a top or upper wall of the casing for actuating the lever to release the clamping effect of the leaf spring.

FIG. 13 is a end elevational view with a portion thereof broken away for clarity, and illustrates details of the pivotal mounting of the lever.

Figure 3:
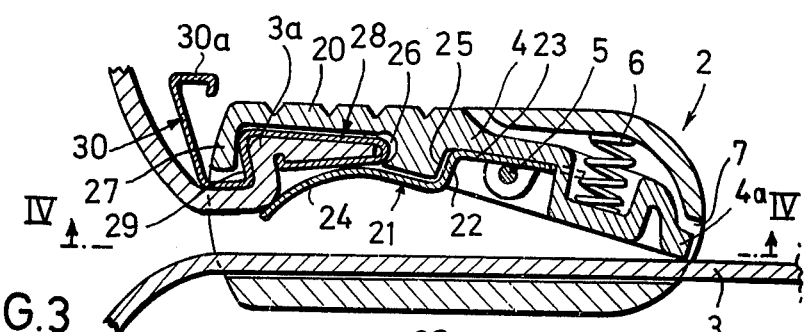
FIG. 3 is an enlarged fragmentary sectional view taken generally along line III—III of FIG. 2 and more clearly illustrates details of a fitment secured to an end of the band and a generally Z-shaped leaf spring which secures the fitment to the clamping lever.
Figure 4:
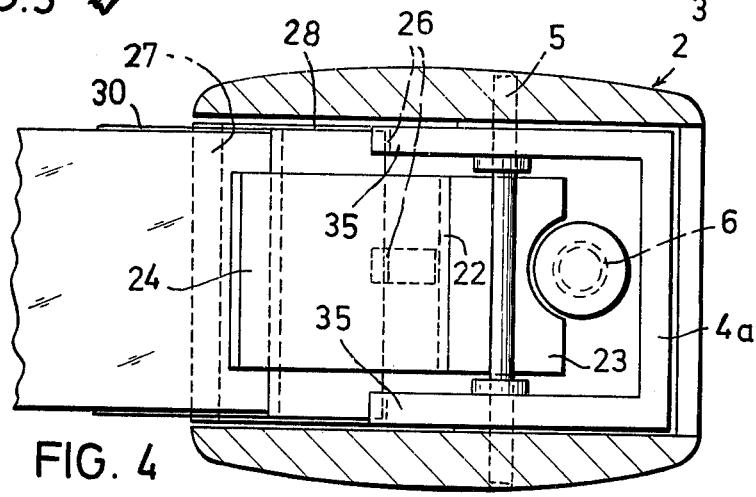
FIG. 4 is a cross sectional view taken generally along line IV—IV of FIG. 3, and illustrates details of the underside of the spring.

A novel ligature or ligature mechanism constructed in accordance with this invention is generally designated by the reference numeral 1 and includes a casing or housing 2 having an aperture 7 through which passes an end portion 3a of a band 3 which includes a loop portion 3b and another terminal end portion 3c. A clamping lever 4 is mounted by a pivot pin 5 which spans side walls (unnumbered) of the casing 2, as is best illustrated in FIG. 4. The clamping lever 4 includes a conventional press button portion 20 and is normally biased toward its locked position (FIG. 3) by a spring 6 such that a nose 4a of the clamping lever 4 bears against the band 3 and clamps the same against a lower wall (unnumbered) of the casing 2.

Spring means in the form of a generally Z-shaped leaf spring 21 is carried by the clamping lever 4 and has a width generally corresponding though slightly narrower than the distance between depending side walls 35, 35 of the clamping lever 4, as is best illustrated in FIG. 4. A central portion 22 of the leaf spring 21 bears against a shoulder 25 of the clamping lever 4 while a leg 23 of the spring 21 is held under tension between the pivot pin 5 and an undersurface (unnumbered) of the clamping lever 4. An opposite end or leg 24 of the spring 21 forms a spring flap curved to open concavely downwardly, and due to the inherent tension of the spring 21, the central portion 22 is normally in engagement with a shoulder 25 of the clamping lever 4.

A recess 26 is formed at an underside of a pressbutton portion 20 of the clamping lever 4 and defines in conjunction with the spring flap 24 a recess or insertion slot which opens generally in a direction away from the aperture 7 and toward the loop 3b for the receipt of a fitment 28 secured to the terminal end portion 3a of the band 3. The fitment 28 is preferably constructed from metal and includes a stop portion 29 and a tab 30 inclined upwardly and rearwardly toward the loop 3b, as viewed in FIG. 3 with the tab 30 terminating in a projecting portion 30a directed generally toward the forward end of the casing 2 defined by that end (unnumbered) having the aperture 7 formed therein. The tab 30 is considered means for releasing the integral fitting means 28 of the terminal end portion 3a in a manner to be described more fully hereinafter. A portion 29 of the fitting 28 bears against abutment means in the form of a shoulder or wall 27 which depends downwardly from the push-button portion 20 of the clamping lever 4. In this manner, the fitting portion or fitting 28 is confined between the abutment means 27, the slot or groove 26 and the flap 24 of the spring 21 in the clamped position shown best in FIG. 3.

In order to release the terminal end portion 3a of the band 3 from the housing 2, it is simply necessary to depress the portion 30a of the releasing means or tab 30 which bends the flap 24 of the spring 21 downwardly causing the wall 29 to ride downwardly beyond the abutment means or abutment wall 27. Upon the latter occurrence, the end 3a of the band is free and the ligature mechanism 1 can be readily removed from the limb to which it was applied.

In accordance with the embodiment of the invention illustrated in FIGS. 1 through 4, it is essential that both of the push-button portion 20 of the lever 4 for raising the nose 4a upon the depression of the push-button 20 and the actuation of the tab 30a occurs simultaneously and by the same finger, preferably the thumb of one hand, so that they can only be released one after the other and accidental pressure on the tab 30 during the tourniquet effect is eliminated. This safety measure against unintentional or inadvertent release of the terminal end 3a of the band 3 is further reinforced by the fact that the tab 30 extends obliquely toward the loop 3b in an upward direction so that when the ligature mechanism 1 is applied to a limb the tab 30 bears on the limb so that the limb forms a countersupport against the depression of the tab 30 which is increasingly effective, particularly upon actuation of the press-button portion or press button 20.

Figure 5:
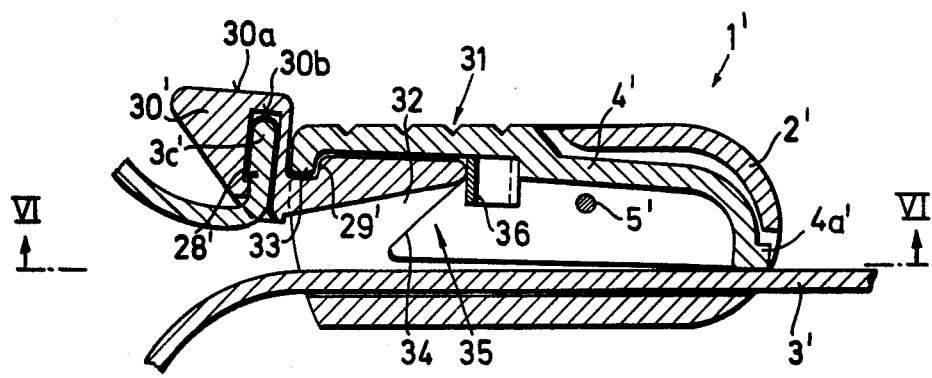
FIG. 5 is a fragmentary longitudinal sectional view of another ligature mechanism constructed in accordance with this invention and illustrates an end of a band snap-connected to a fitting which in turn is snap-connected to a clamping lever.
Figure 6:
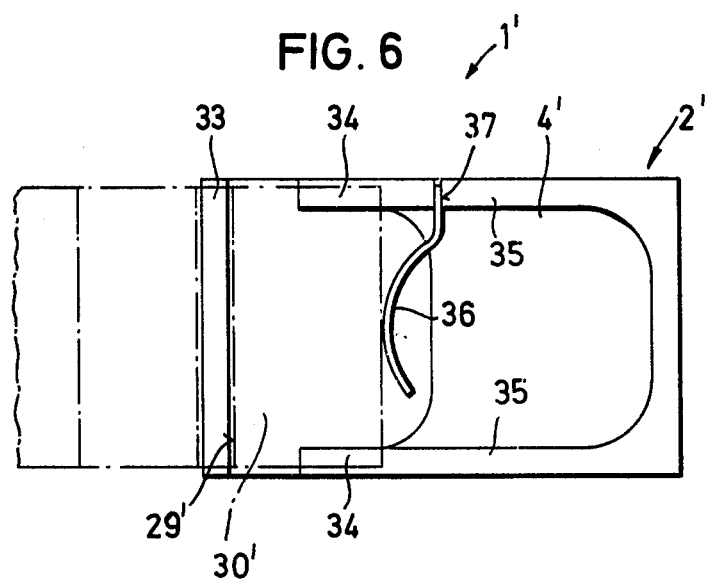
FIG. 6 is a sectional view taken generally along line VI—VI of FIG. 5, and illustrates details of the leaf spring.

Reference is now made to FIGS. 5 and 6 of the drawings in which like reference numerals though primed correspond to components of the ligature mechanism 1 of FIGS. 1 through 4. In the ligature mechanism 1' of FIGS. 5 and 6, the fitment and releasing means are of a one-piece construction. In this case, a tab, fitment or projection 30' is provided with a recess or slot 30b which snap-engages a fitment portion 28' secured to a terminal end portion 3c' of the band 3'. The clamping lever 4' includes a push-button portion 31 on the underside of which is a recess 32 defined in part by abutment means in the form of an abutment wall 33. The clamping lever 4' further includes depending side walls 35, 35 (FIG. 6) having obliquely inclined edges 34 (FIG. 5) and spanning the side walls 35, 35 in the area of the oblique edges 34 adjacent the recess 32 is a leaf spring 36 having an end portion 37 tightly received in a slot (unnumbered) of one of the side walls 35. Thus, a portion (unnumbered) of the fitment 30' is received in the recess 32 in sandwiched relationship between the abutment means 33 and the spring 36 and is held thereat by the spring 36. That portion of the fitment 30' which lies in the recess 32 has a transverse width greater than the distance between the oblique walls 34, as is most readily apparent from FIG. 6 of the drawings. Thus, in order to release the fitment portion from the recess 32, a finger portion 30a is depressed causing the spring 36 to deflect until such time as the shoulder (unnumbered) passes beneath and beyond the abutment means 33. At this point the fitment 30' can be removed from the casing 2'.

The purpose of the inclined surfaces 34 is to avoid the necessity of the spring 6 of the ligature device 1 of FIGS. 1 through 4. Due to the inclined surfaces 34 that portion of the fitting 30' within the recess 32 bears or rides along the surfaces 34 and the spring 36 urges the same generally upwardly causing the nose 4a' to pivot downwardly or stated otherwise, the clamping lever 4' is automatically pivoted in a clockwise direction to effect a clamping effect between the band 3' and the lower wall (unnumbered) of the housing 2'. In order to facilitate this automatic biasing of the clamping lever 4' in a clockwise direction, the slot 37 is preferably disposed at an oblique angle such that when the portion of the fitting 30' which is received in the slot 32 is fully seated therein a component of the biasing force of the spring 36 will also act to bias the clamping lever 4' in a clockwise direction.

Figure 1:
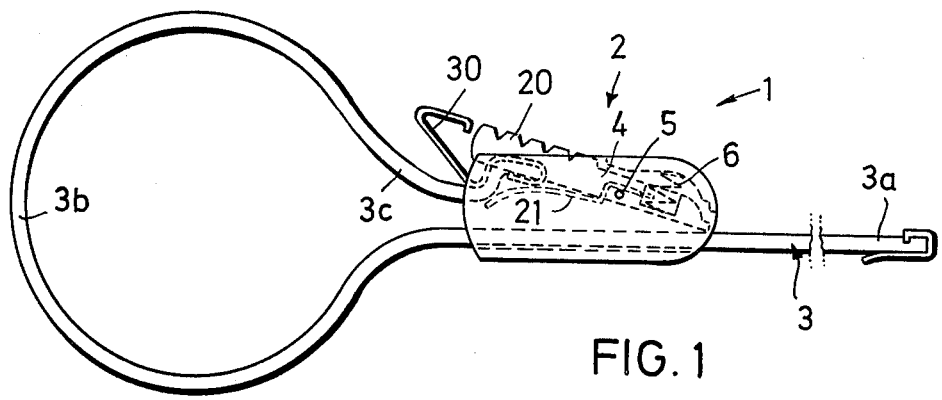
FIG. 1 is a side elevational view of a novel ligature mechanism constructed in accordance with this invention, and illustrates a housing carrying a clamping lever with one end of a band attached thereto and another end passing through to an aperture of the casing.
Figure 2:
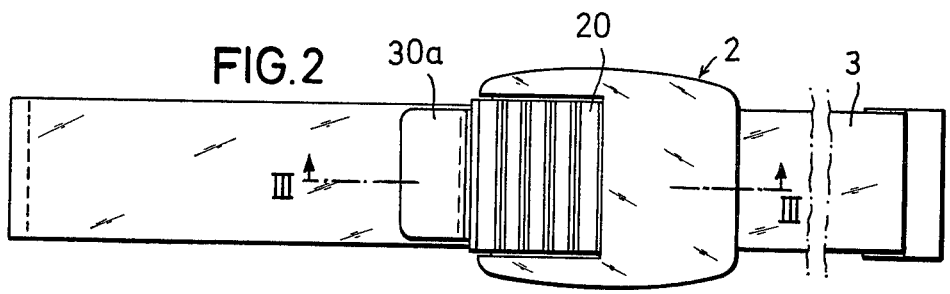
FIG. 2 is a top plan view of the ligature mechanism of FIG. 1 and illustrates means for releasing the band from the clamping lever with the releasing means being an integral portion of a fitting clamped to a terminal end of the band.

In another embodiment of this invention illustrated in FIGS. 7 and 8, like structure corresponding to that shown in FIG. 1 has been double-primed, but in this case, the spring means, though it is a leaf spring 8 is not carried by the clamping lever 4" but instead is disposed adjacent a lower wall (unnumbered) of the casing 2'. The leaf spring 8 includes a transverse groove 10 opening upwardly and spanned by a pin 11 housed in openings (unnumbered) of the side walls (also unnumbered) of the casing 2". The pin 11 and groove 10 thus define means for securing the spring 8 to the casing 2". The spring 8 is also a leaf spring but is of an undulating configuration and has a depending projection 9 which in the locked position (FIG. 7) engages against the terminal end portion 3c' of the band 3" to preclude the release thereof from the casing 2" until release means in the form of a button 13 is pushed upwardly. The clamping lever 4" is, of course, shown in its unlocked position as though it were held by an unillustrated finger, and when released the spring 6 would simply effect the same locking as shown in FIGS. 3 and 5.

Reference is now made to FIGS. 9 and 10 of the drawings in which a casing 2''' is identical to the casing 2" of FIG. 7 except for the absence of the spring 6" and the fact that in lieu of the release means 13 of FIG. 7 a lever 14 is provided which when lifted by a tab 14a will raise the projection 9 to permit the unillustrated terminal end portion of the unillustrated band to be removed from the casing.

In FIGS. 11 through 13 a casing 2'''' is generally identical to the casing 2" of FIG. 7 along with the securing means 10, 11 of the latter for the leaf spring 8''''. However, the release means in this embodiment of the invention constitutes a lever 15 having a laterally extending leg 17 which underlies the spring 8'''' and another laterally extending end 16 which projects through an aperture (unnumbered) of the casing 2''''. Upon depressing the projection or extension 16, the lever 15 is pivoted in a clockwise direction to release the locking function of the projection 9''''.

While preferred forms and arrangements of parts have been shown in illustrating the invention, it is to be clearly understood that various changes in details and arrangement of parts may be made without departing from the scope and spirit of this disclosure.

I claim:

1. A ligature mechanism for producing tourniquet effects on limbs comprising a casing, a clamping lever, means mounting said clamping lever for pivotal movement relative to said casing, a band, said band including first and second terminal end portions and a loop portion therebetween, aperture means in said casing for permitting the passaage of said first terminal end portion through said casing, a portion of said band between said loop and said first terminal end portion being clamped relative to said casing by said clamping lever, fitting means carried by said second terminal end portion, spring means releasably clampingly securing said second terminal end portion fitting means to said lever, and means for releasing the clamping effect of said spring means to release said second terminal end portion from said clamping lever.

2. The ligature mechanism as defined in claim 1 wherein said spring means is a leaf spring.

3. The ligature mechanism as defined in claim 2 wherein said clamping lever includes a top wall and opposite side walls, and said opposite side walls have upper edges angling downwardly away from said top wall and in a direction away from said aperture means.

4. The ligature mechanism as defined in claim 2 wherein said clamping lever includes a top wall and opposite side walls, a slot in one of said side walls, and said leaf spring has a terminal end received in said slot.

5. The ligature mechanism as defined in claim 1 wherein said spring means is a leaf spring, said leaf spring includes a free terminal end portion, and said releasing means is operative against said leaf spring inboard of said free terminal end portion.

6. The ligature mechanism as defined in claim 1 wherein said releasing means is an integral extension of said fitting means.

7. The ligature mechanism as defined in claim 6 wherein said releasing means and said fitting means are formed as a single piece of plastic material.

8. The ligature mechanism as defined in claim 7 wherein said abutment means includes a depending abutment wall, and said fitting means includes a slot for receiving said abutment wall.

9. The ligature mechanism as defined in claim 1 wherein said clamping lever includes abutment means in opposed spaced relationship to said spring means, and said fitting means is sandwiched between said abutment means and said spring means and is released from the latter sandwiched relationship upon the actuation of said releasing means.

10. The ligature mechanism as defined in claim 9 wherein said abutment means includes a depending abutment wall, and said fitting means includes a slot for receiving said abutment wall.

11. The ligature mechanism as defined in claim 1 wherein said clamping lever includes abutment means in opposed spaced relationship to said spring means, said fitting means is sandwiched between said abutment means and said spring means and is released from the latter sandwiched relationship upon the actuation of said releasing means, and said spring means is a leaf spring having a terminal end portion projecting toward said abutment means.

12. The ligature mechanism as defined in claim 1 wherein said clamping lever includes abutment means in opposed spaced relationship to said spring means, said fitting means is sandwiched between said abutment means and said spring means and is released from the latter sandwiched relationship upon the actuation of said releasing means, said spring means is a leaf spring having a terminal end portion projecting toward said abutment means, and said releasing means is an integral extension of said fitting means.

13. The ligature mechanism as defined in claim 1 wherein said clamping lever includes abutment means in opposed spaced relationship to said spring means, said fitting means is sandwiched between said abutment means and said spring means and is released from the latter sandwiched relationship upon the actuation of said releasing means, said spring means is a leaf spring having a terminal end portion projecting toward said abutment means, and said releasing means is an integral extension of said fitting means projecting past said abutment means outwardly of said casing.

14. The ligature mechanism as defined in claim 1 wherein means are provided for snap connecting said fitting means to said clamping lever.

15. The ligature mechanism as defined in claim 1 wherein said clamped portion of said band includes a longitudinal axis, said spring means is a leaf spring, and said leaf spring is carried by said clamping lever in transverse relationship to said longitudinal axis.

16. The ligature mechanism as defined in claim 1 wherein means are provided for snap connecting said fitting means to said clamping lever, said clamping lever includes abutment means in opposed spaced relationship to said spring means, and a first portion of said releasing means is sandwiched between said abutment means and said spring means and is released from the latter sandwiched relationship upon the actuation of a second portion of said releasing means exterior of said casing.

17. The ligature mechanism as defined in claim 1 wherein means are provided for snap connecting said fitting means to said clamping lever, said clamping lever includes abutment means in opposed spaced relationship to said spring means, a first portion of said releasing means is sandwiched between said abutment means and said spring means and is released from the latter sandwiched relationship upon the actuation of a second portion of said releasing means exterior of said casing, said clamped portion of said band includes a longitudinal axis, said spring means is a leaf spring, and said leaf spring is in transverse relationship to said longitudinal axis.

18. The ligature mechanism as defined in claim 1 wherein said releasing means and said fitting means are formed as a single piece of plastic material.

* * * * *